United States Patent
Simmons et al.

(10) Patent No.: US 8,981,316 B2
(45) Date of Patent: Mar. 17, 2015

(54) RADIATION STERILIZATION OF IMPLANTABLE MEDICAL DEVICES

(75) Inventors: Gregory Scott Simmons, Temecula, CA (US); Brian Riggs, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 805 days.

(21) Appl. No.: 12/753,830

(22) Filed: Apr. 2, 2010

(65) Prior Publication Data

US 2011/0240882 A1  Oct. 6, 2011

(51) Int. Cl.
*G01N 23/00* (2006.01)
*A61L 2/08* (2006.01)
*A61L 2/24* (2006.01)

(52) U.S. Cl.
CPC . *A61L 2/08* (2013.01); *A61L 2/087* (2013.01); *A61L 2/24* (2013.01)
USPC .................................. 250/455.11; 250/492.1

(58) Field of Classification Search
USPC ......................................... 250/453.11, 454.11
See application file for complete search history.

(56) References Cited

U.S. PATENT DOCUMENTS

| | | | | |
|---|---|---|---|---|
| 695,116 A * | 3/1902 | Ohmer et al. | ..................... | 101/66 |
| 795,857 A * | 8/1905 | Prentice | ........................... | 246/30 |
| 3,916,204 A * | 10/1975 | Swartz | ..................... | 250/453.11 |
| 5,226,065 A * | 7/1993 | Held et al. | ....................... | 378/64 |
| 5,661,305 A * | 8/1997 | Lawrence et al. | ............. | 250/397 |
| 6,215,847 B1 | 4/2001 | Perrins et al. | | |
| 6,376,845 B1 * | 4/2002 | Purtle | ........................ | 250/491.1 |
| 6,617,596 B1 * | 9/2003 | Korenev | ..................... | 250/492.3 |
| 6,713,773 B1 * | 3/2004 | Lyons et al. | ................ | 250/492.3 |
| 6,806,476 B2 | 10/2004 | Rose et al. | | |
| 6,949,222 B1 * | 9/2005 | Moller et al. | ..................... | 422/62 |
| 7,175,806 B2 * | 2/2007 | Deal et al. | ......................... | 422/24 |
| 7,588,803 B2 * | 9/2009 | Demos et al. | .................. | 427/551 |
| 2003/0039579 A1 * | 2/2003 | Lambert et al. | .................. | 422/22 |
| 2003/0128807 A1 * | 7/2003 | Kotler et al. | ..................... | 378/64 |
| 2003/0136920 A1 * | 7/2003 | Flores et al. | .............. | 250/455.11 |
| 2004/0217300 A1 | 11/2004 | Loda | | |
| 2005/0178977 A1 * | 8/2005 | Koenck et al. | ........... | 250/455.11 |
| 2006/0192140 A1 * | 8/2006 | Nablo et al. | ................ | 250/492.1 |
| 2007/0114432 A1 * | 5/2007 | Kristiansson et al. | ........ | 250/397 |
| 2007/0280851 A1 | 12/2007 | Freeman et al. | | |
| 2008/0010947 A1 | 1/2008 | Huang et al. | | |
| 2008/0044553 A1 * | 2/2008 | Freeman et al. | .............. | 427/2.24 |
| 2009/0074610 A1 * | 3/2009 | Sabaria | ........................... | 422/23 |
| 2010/0001206 A1 * | 1/2010 | Maxim et al. | ............ | 250/455.11 |
| 2011/0020174 A1 * | 1/2011 | Rauschnabel et al. | .......... | 422/22 |

FOREIGN PATENT DOCUMENTS

| | | |
|---|---|---|
| JP | 2000-334028 | 12/2000 |
| WO | WO 02/061464 | 8/2002 |
| WO | WO 03/009875 | 2/2003 |

OTHER PUBLICATIONS

International Search Report for PCT/US2011/029815, mailed May 31, 2011, 5 pgs.

* cited by examiner

*Primary Examiner* — Jack Berman
*Assistant Examiner* — Jason McCormack
(74) *Attorney, Agent, or Firm* — Squire Patton Boggs (US) LLP (57) ABSTRACT

A system and method for sterilization of medical devices includes methods for reducing the variance in dose levels over the medical device by either varying the dose levels for each pass before a radiation source, such as an electron beam, or by increasing the number of passes before a radiation source.

12 Claims, 5 Drawing Sheets

RADIATION STERILIZATION OF IMPLANTABLE MEDICAL DEVICES

BACKGROUND OF THE INVENTION

1. Field of the Invention

The present invention relates to a medical device; more particularly, this invention relates to methods of sterilizing the medical device by irradiation of the medical device.

2. Background of the Invention

Systems for sterilizing products such as food or mail to remove harmful micro-organisms are known in the art. Such a system may operate as a conveyor in which products are carried pass a radiation source where the product is subjected to a predetermined dose of radiation, e.g., X-ray, gamma or electron radiation, at a predetermined level or intensity. Careful and continuous control of the dose delivered to a product is critical. If a product receives too little radiation, the desired sterilization, pasteurization, and/or chemical modification is not obtained. If a product receives too much radiation, the treatment is damaging to the product.

It is known to expose a product to two passes before a radiation source to ensure adequate sterilization, or rotating the product within the radiation field. U.S. Pat. No. 6,806,476 discloses a radiation conveyor system operated to cause a product on the conveyor to make two passes before the radiation source, e.g., an electron beam. The product is flipped 180 degrees between first and second passes. The system exposes the product to a predetermined level of radiation defined by, among other things, a dose level, beam width, speed of conveyor selected and electron energy spread spectrum.

For products that are particularly dense, the art has configured systems, such as the one described in U.S. Pat. No. 6,806,476, to perform two passes before the radiation source. The first pass may place the product broad side before the radiation source. Then the product is flipped 180 degrees around and again passed broad side before the radiation source. This ensures a minimum dosage level is applied to the product to ensure sterility. The same dose level is used for both passes.

Sterilization of implantable medical devices by exposure to radiation is known. Sterilization is typically performed on implantable medical devices, such as stents and catheters, to reduce the bioburden on the device. Bioburden refers generally to the number of microorganisms that contaminate an object. The degree of sterilization is typically measured by a Sterility Assurance Level ("SAL"), referring to the probability of a viable microorganism being present on a device unit after sterilization. A sterilization dose can be determined by selecting a dose that provides a required "SAL". The required SAL for a device is dependent on the intended use of the device. For example, a device to be used in the body's fluid path is considered a Class III device. SALs for various medical devices can be found in materials from the Association for the Advancement of Medical Instrumentation (AAMI) in Arlington, Va. For example, the SAL for biodegradable stents is at a radiation dose from about 20 kGy to about 30 kGy. The required dosage depends upon the starting bioburden in the medical device, which can vary based on the degree of sterility maintained when the medical device is fabricated.

Medical devices composed in whole or in part of polymers can be sterilized by various kinds of radiation, including, but not limited to, electron beam (e-beam), gamma ray, ultraviolet, infra-red, ion beam, and x-ray sterilization. A sterilization dose can be determined by selecting a dose that provides a required SAL. One problem faced in the art is how to apply sufficient radiation to achieve the SAL without causing degradation to bio-absorbable polymers and/or therapeutic agents contained within a polymer coating. High-energy radiation tends to produce ionization and excitation in polymer molecules, as well as free radicals. These energy-rich species undergo dissociation, abstraction, chain scission and cross-linking in a sequence leading to chemical stability. The stabilization process can occur during, immediately after, or even days, weeks, or months after irradiation which often results in physical and chemical cross-linking or chain scission. Resultant physical changes can include embitterment, discoloration, odor generation, stiffening, and softening, among others. In particular, the deterioration of the performance of polymeric materials and drugs due to e-beam radiation sterilization has been associated with free radical formation in a device during radiation exposure and by reaction with other parts of the polymer chains. The reaction is dependent on, e.g., e-beam dose and level of temperature.

For these reasons, sterilization procedures for medical devices containing polymers and/or radiation-sensitive drugs specify an upper limit to the dose levels that the medical device may accept without degrading the performance of the product. As the actual upper limit to ensure the medical device does not degrade, or lower limit to ensure sterility is an approximation, the lower dose range and upper dose range often includes safety factors, which narrows the operating range for sterilization. This complicates the sterilization process and limits the range of designs or materials available for medical devices.

Accordingly, there is a continuing need for improvement in the processes for sterilization of medical devices containing polymers and/or therapeutic drugs that are adversely affected by over-exposure to radiation.

SUMMARY OF THE INVENTION

The invention provides methods and systems for radiation sterilization of a medical device formed in whole, or in part, by a polymer material and medical devices containing radiation-sensitive therapeutic agents. Preferably, e-beam sterilization is used, however other radiation sterilization sources may be used without departing from the scope of the invention.

The method and systems described herein are especially adapted for improving a sterilization process for implantable medical devices. The methods and systems are particularly relevant to implantable medical devices having a polymeric substrate, a polymer-based coating, and/or a drug-delivery coating. A polymer-based coating may contain, for example, an active agent or drug for local administration at a diseased site. An implantable medical device may include a polymer or non-polymer substrate with a polymer-based coating.

One example of an implantable medical device particularly suited for radiation sterilization according to the invention is a drug-eluting polymer stent. It has been observed that e-beam radiation of polymer stents can result in cracking of struts during deployment due to onset of brittle behavior. The cracking can be due to a reduction in molecular weight. Additionally, the increase in temperature can result in a loss of some or all of the induced orientation and strength due to relaxation of polymer chains. Furthermore, radiation, which increases the temperature of the stent, can increase the release rate of drug resulting in a decrease of drug loading on a stent. Therefore, the modification of polymer properties due to radiation is generally due the reactions which are chemical in nature as well as the increase in temperature of a sample. Thus, by reducing the dose level at any location on the medical device, there will be reduced rate of loss of molecular weight, or greater control over molecular weight loss, and/or alterations in the release rate of a drug contained within a polymer coating. Accordingly, greater control and predictability over the performance of the polymer stent when implanted within a body is possible when practicing the methods of the invention.

The problems in the art addressed by the invention are two-fold, but related. Typical bioburden levels for an implantable medical device require at least 25 kGy to reduce the bioburden on the device to the required SAL of $10^{-6}$. In prior years, the upper limit for radiation dosages has been upwards of 100 kGy. This afforded a wide operating range for making adjustments or operating the radiation source, e.g., an electron beam, without requiring precise control over beam parameters, conveyor speed, etc. More recent trends in medical devices, especially the development of drug-eluting bio-absorbable polymer stents (as described above), however, have required the upper dose limit to be significantly lowered to avoid causing damage to the device. Typical upper ranges for a drug-eluting bio-absorbable polymer stent are now 30 kGy or less. This significantly reduces the available operating range, which increases the complexity of the sterilization procedure because greater control over the speed of the device as it passes through the radiation source, and beam parameters is required. Similarly, the more narrow range required now makes it more difficult to maintain a sufficient level of throughput, i.e., time required to sterilize each device. Moreover, when operating within more narrow ranges, even assuming more precise control is feasible, there is greater risk that the maximum allowable dose will be exceeded since dose levels approach upper limits more often than in the past.

In view of the foregoing, methods are provided to reduce variance in radiation dosages received over a medical device by adjusting dosage levels with orientation of the medical device relative to a radiation source. For example, for a first pass the medical device is disposed in a first orientation, e.g., front facing the radiation source, and then exposed to radiation at a first dose level. For a second pass the medical device is disposed in a second orientation, e.g., back facing the radiation source, and then exposed to radiation at a second dose level, different from the first dose level. The dose levels are selected so as to arrive at a total radiation exposure, meaning the sum total of radiation received when the first dose is administered and the radiation received when the first dose is administered, for the medical device that best minimizes differences between doses received at different locations on the medical device. With variance in dose minimized over the device, there is a greater operating range made available, which simplified the sterilization process and reduces instances where does levels approach maximum allowable limits for the device.

Moreover, with a wider operating range available a process for radiation sterilization may achieve higher throughput by obviating or reducing the need to undertake special measure to reduce radiation damage. When the upper range of the radiation dose is close to the upper limit for the medical device, more control is needed in order to assure that no damage occurred, even if the upper limit is not reached, which makes the sterilization process for each medical device more time consuming. For example, temperature controls have been proposed as a measure to avoid glass transition temperatures from being reached within the polymer material due to radiation, see e.g., US Pub. No. 2008/0010947.

According to one aspect of the invention, a method for sterilizing a medical device by irradiation, includes the steps of obtaining a first dose map and a second dose map for the medical device based on exposure of the medical device to a nominal dose level. The dose maps are obtained, respectively, by disposing the medical device in a first orientation relative to a radiation source to obtain the first dose map, and disposing the medical device in a second orientation relative to the radiation source to obtain the second dose map. Next, the method includes the steps of selecting a first dose level and a second dose level based on a distribution of dose levels described by each of the first dose map and the second dose map; and sterilizing the medical device including the steps of disposing the medical device in the first orientation and then exposing the medical device to the first dose level and disposing the medical device in the second orientation and then exposing the medical device to the second dose level, wherein a total radiation received at a location on the medical device is the sum total of the radiation received at the location after exposure to the first dose and the second dose.

The first dose level and the second dose level are selected so that the difference in total radiation throughout the product is minimized. The method may further include the step of disposing the medical device in additional orientations relative to a radiation source and exposing the medical device to different dose levels to obtain a additional dose map, and the sterilizing step further includes disposing the medical device to the additional orientations and then exposing the medical device to the corresponding dose level. For example, three orientations and three passes, as opposed to two, may be used. Also, the first dose level may be reduced relative to the second dose level when a first density of material in a high dose area for the first orientation is higher than a second density of material in a high dose area for the second orientation.

In accordance with another aspect of invention, a system for sterilizing a medical device by irradiation includes a radiation source; a conveyor system for moving a plurality of devices before the radiation source in conjunction with the dose levels of radiation desired per device; providing a first and second dose level to use when the device is respectively, orientated in a first and second orientation on the conveyor before the radiation source, the dose levels be different from each other; and sterilizing a plurality of such medical devices including the steps of disposing the medical devices in the first orientation on the conveyor and then exposing the medical devices to the first dose level and then disposing the medical device in the second orientation on the conveyor and then exposing the medical devices to the second dose level.

In accordance with another aspect of invention, a method for sterilizing a medical device by irradiation includes the steps of obtaining a first dose map, a second dose map and a third dose map for the medical device based on exposure of the medical device to a nominal dose level; sterilizing the medical device including the steps of disposing the medical device in the first orientation and then exposing the medical device to a first dose level, disposing the medical device in the second orientation and then exposing the medical device to a second dose level and disposing the medical device in the third orientation and then exposing the medical device to a third dose level. The method may include selecting a first dose level, second dose level and a third dose level based on a distribution of dose levels described by each of the first dose map, second dose map and third dose map. The first, second and third dose levels may also be the same.

In accordance with another aspect of invention, a method for sterilizing a medical device by irradiation includes the steps of (1) obtaining N dose maps for a medical device based on exposure of the medical device to a nominal dose level when the device is orientated in a respective N different directions relative to a radiation source; and (2) sterilizing the medical device including the steps of disposing the medical device in the N different directions and then exposing the medical device to a respective N dose levels for each of the N directions;

The N dose level and/or N directions are selected so that the difference in total radiation throughout the medical device is minimized. Alternatively, the N dose level and/or N directions may be chosen to minimize the differences between a minimum and a maximum dose, e.g., difference between two dosimeter readings, as opposed to an overall minimization of differences. In some embodiments the N dose levels may be the same. In other embodiments, both the dose levels and the orientations are adjusted to produce a minimal variance. The integer N may be less than 10, or 2, 3, 4 or 6. The dose levels may be adjusted for one or more of the N orientations according to the density of material in a high dose zone for the respective orientation relative to the other orientations.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 2 is a schematic illustrating a density profile for a medical device having a circular cross-section. In this example, the areas of high density are modeled as a triangle, i.e., three high density sides. When determining the optimum number of passes the shaped formed by the majority of the mass is more important than the overall shape. For this density profile of the medical device, three passes are made before a radiation source. Each pass orients the device at 120 degree increments relative to the radiation source.

FIGS. 3A-3C show radiation levels when the same dose level is used for each pass. FIGS. 4A-4C shows the radiation dose level when dose levels according to the invention are used to minimize the variance in dose levels over the device.

FIGS. 5A-5C show radiation levels after two passes when the same dose level is used for each pass. FIGS. 6A-6C shows radiation levels when the device is oriented in three different directions for three different passes before the radiation source.

DETAILED DESCRIPTION OF EMBODIMENTS

Figure 1:
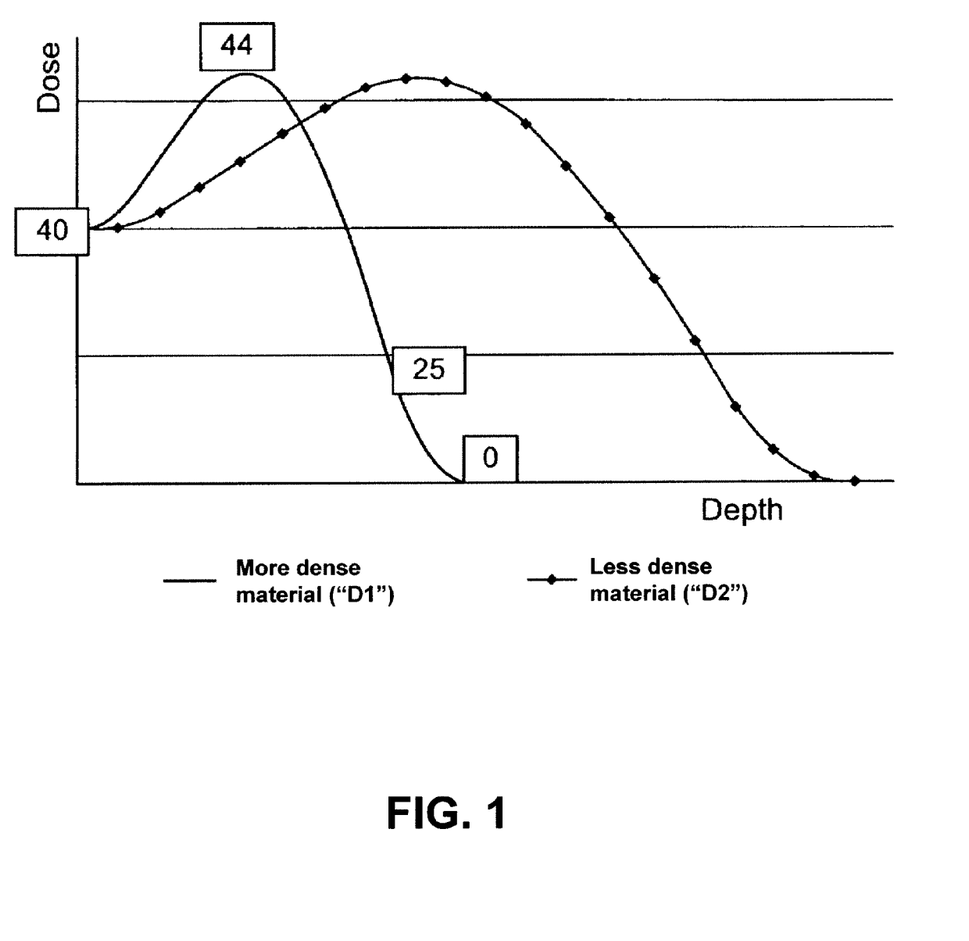
FIG. 1 is depth-distribution curve which depicts the relationship between the dose level received for a material having a first density (D1) and a second density (D2).

FIG. 1 depicts a depth dose distribution curve illustrating the relationship between radiation exposure and depth of penetration of a radiation beam for materials with two densities. The curve shows the dose versus the depth of a material that the electrons travel through for two different densities, a higher density D1 and lower density D2. As depicted, the dose initially rises, then drops off, in each case. When the material is more dense, e.g., D1, the ramp up is more rapid and the decline in dose level verses depth is more rapid. For example, if a device is characterized as having the density D1 is irradiated with 40 kGy, the peak dose is at 44 kGy, and eventually drops down to, for example, 25 kGy and finally to 0 kGy upon further permeation through a material. The sharp ramp-up near the front face of the material having the higher density may be explained, at least in part, by the increased frequency of collisions between the incoming electrons and the denser material near the front face. This rapidly increases the dosage until it reaches a peak (44 kGy) then drops off sharply as the number of electrons penetrating through to deeper depths decreases. When the material is less dense, i.e., D2, the peak is reached more gradually and the distribution of dosage more uniform since there is less collisions with the material initially, so that there are a greater number of electrons penetrating deeper into the material.

According to the disclosure, methods are provided to reduce variance in radiation dosages received over a medical device by adjusting dosage levels with orientation of the medical device relative to a radiation source. A method according to the invention may include the following steps. First, the device is characterized by a density profile, which describes the distribution of mass, or density for the device. The density profile indicates the number of passes before the radiation source, e.g., 2, 3 or more, and the orientation of the device relative to the radiation source for each pass. Next, an independent dose map is made for each pass. Then, after obtaining the dose maps, a dose level is derived for each pass. The dose levels are selected to minimize the difference, or variance between the sum total of the radiation levels received at different locations on the medical device after all passes before the radiation source. In some embodiments, the density profile determination step or dose level determination step is not needed, or they are readily apparent.

As discussed in connection with FIG. 1, variances in radiation dosage across a device are expected to be more extreme in areas where there is more mass, or higher density of material. Thus, where the material is the most dense one expects the greatest variance in dosage levels. The less dense material receives a more uniform dose. Accordingly, there is less concern over differences in dosage levels in low density areas. The inventors found that, when determining how best to expose the device to radiation to reduce variances in the dosage, it is sometimes useful to characterize the shape of the device in terms of a polygon that both best describes the distribution of the device's more dense components and indicates the orientations of the device relative to the radiation source to produce a reduction in variance in the dosage level over the device. This "shape" as the same as the density profile mentioned in the prior paragraph.

Figure 2:
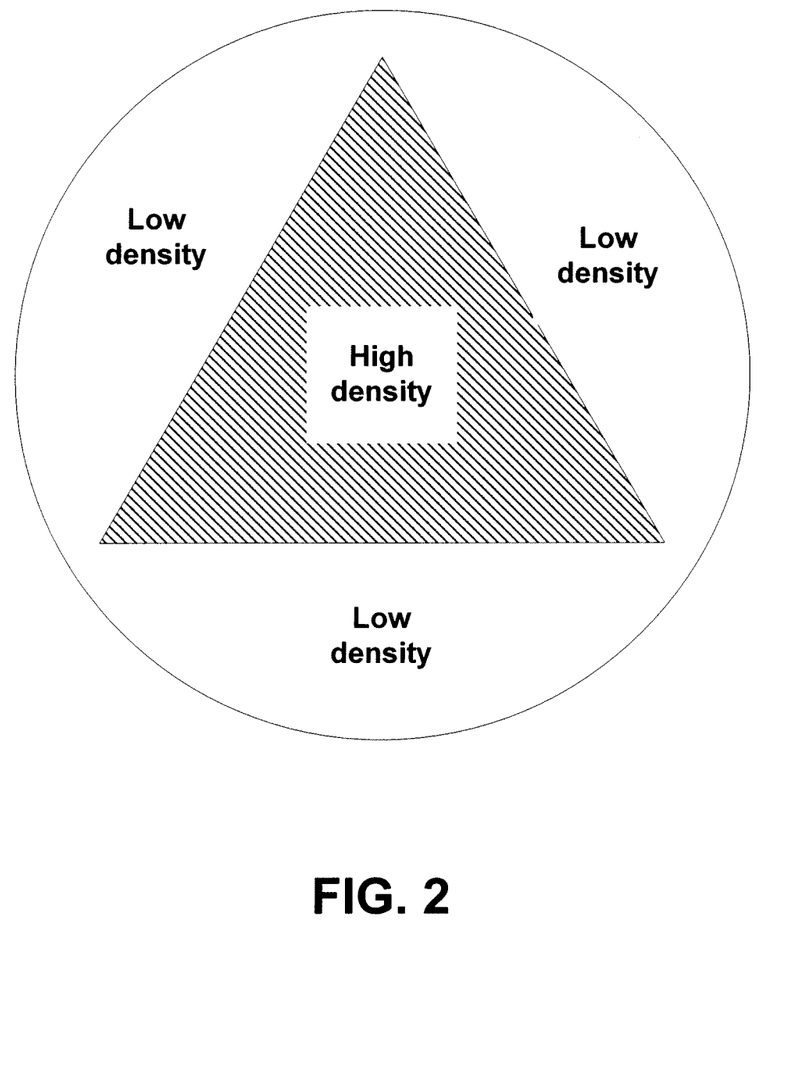

A density profile for a device is illustrated in FIG. 2. A density profile is a polygon, generally, where each side indicates the direction in which the body should face the radiation source, to account for its mass distribution. For a body that has a relatively simple or uniform density, the density profile is rectangular, indicating that two passes at 180 degrees orientations would most likely provide adequate reduction in variance in dosage over the device. In the more general case a density profile may be understood, or expressed in terms of the number of passes for a device before a radiation source and the orientation of the device for each of these passes.

The concept of a density profile may be explained by way of example with a catheter product. This type of medical device includes a polymer balloon, a bio-absorbable stent mounted to the balloon, and a composite delivery catheter portions including distal and proximal shaft portions. These components are all packaged within a sealed bag. The most dense parts of the catheter are typically the distal end (where the balloon and stent are placed, and the proximal end of the catheter shaft, assuming no parts are laid on top of another when facing the radiation source. When laid flat the density distribution of the device may be characterized has a two-sided, rectangular shape or density profile.

Figure 3A:
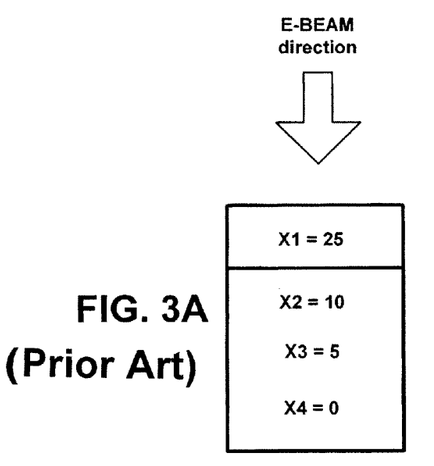
FIGS. 3A-3C and 4A-4C illustrate the distribution of dose levels for a device having a two-sided density profile.

As a further illustration, FIG. 3 depicts a density distribution for a body that has the physical dimensions of a disc but, due to the arrangement of the denser components within the device, its density profile for radiation sterilization is a three-sided polygon. Thus, while the dimensions are circular, the density profile for purposes of facilitating a more uniform exposure to radiation is a three-sided body, or triangle. Accordingly, each of the three sides define three passes before the radiation source, where each pass has the device oriented at 120 degree increments, in the case of an equilateral triangle, for each pass before the radiation source.

With the density profile selected, the next step is to dose map the device for each pass before the radiation source. First, dosimeters are placed at locations over the device to measure the radiation dose received when the device is exposed to a nominal level of radiation. A monitoring dosimeter is placed upstream of the device to measure the level of radiation in the incoming beam. The dose map provides an indication of the relative levels of radiation, relative to the monitoring dosimeter level, that the device will receive when exposed to radiation. A dose map is constructed for each orientation of the device relative to the radiation source. Thus, for a two-sided density profile (e.g., the catheter example, above) two dose maps are constructed. The first with the device facing with its front face facing the radiation source and the second with the device flipped 180 degrees around. For the three-sided density profile of FIG. 3, three dose maps are constructed, with each dose map showing the distribution of radiation received at the locations where dosimeters are placed for each orientation of the device relative to the radiation source.

Dosimeters should be located in places where variances in dose levels can be best realized, e.g., behind a dense component and a less dense component. Dosimeters should also be placed behind more radiation-sensitive material, e.g., a bioabsorbable polymer so that accurate information is available to ensure that maximum dosage levels are not exceeded. After constructing the dose maps, comparison between one dose map and another might indicate that the density profile was improperly constructed. In these cases, different orientations or more orientations/passes of the device before the radiation source may be chosen. Moreover, in cases where it might not be apparent which density profile best characterizes the device for radiation sterilization, an iterative process of dose mapping, followed by comparison of the distribution of dose levels detected by the dosimeters may alternatively be used to selected the best orientations of the device for radiation sterilization.

The next step in the process, which in some embodiments is optional, is determining the dosage level to apply for each pass before the radiation source, so that the variance after all passes is minimized. Existing methods of radiation sterilization, in contrast, use the same dose when two passes before a radiation source is used, e.g., U.S. Pat. No. 6,806,476. However, these systems are not suitable for irradiation of medical devices that require more narrow dose ranges, because the variance in dose levels using the existing methods is too great. It is necessary to reduce this variance so that there is a greater working range made available for sterilizing medical devices containing radiation sensitive material.

The formulation of a density profile, to select the number of passes and orientation of the device for each pass, and comparison of the dose maps for each orientation provides the information for determining the dose level for each pass that will produce the least variance in dose level. With this data available from the dose maps for each pass, one can solve for the dose levels that will produce the minimum variance in dosage everywhere after all three passes. One of ordinary skill will appreciate that there are numerous mathematical methods of minimization available for finding a solution to variance problems posed in this way. Accordingly, they need not be elaborated upon here.

Figures 5A, 5B, 5C:
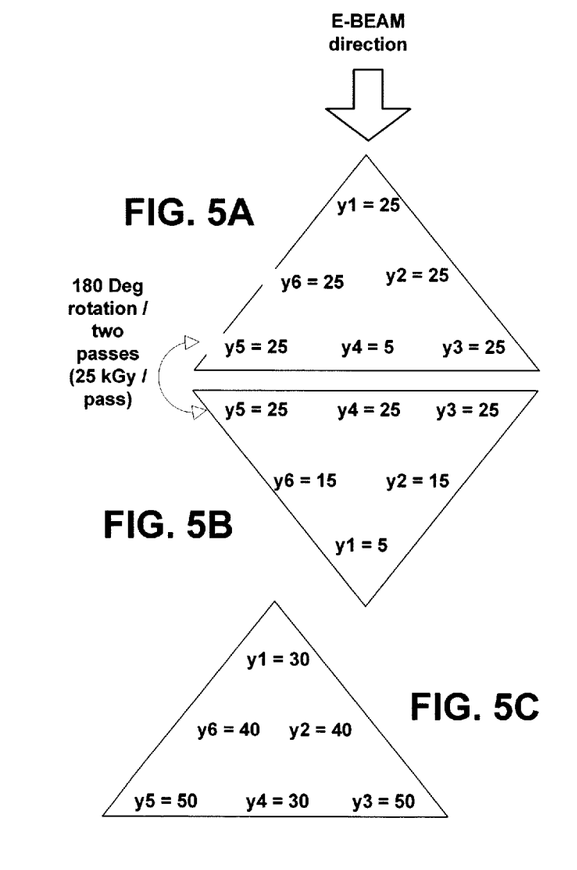
FIGS. 5A-5C and 6A-6B illustrate the distribution of dose levels for the device of FIG. 2 having a three-sided density profile.
Figure 6A:
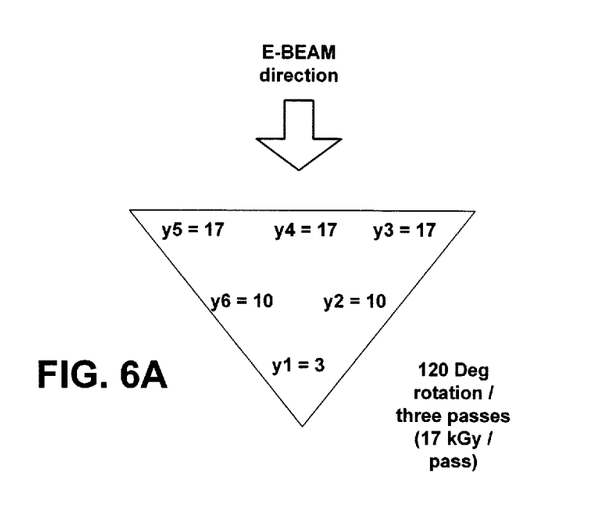
Figure 6B:
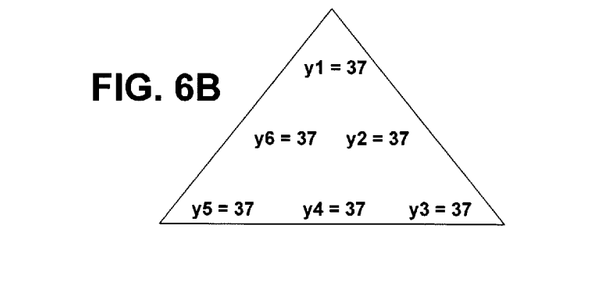

For purposes of illustration, examples for devices characterized by two-sided and three-sided density profiles is provided. In the first example, FIGS. 3 and 4, it is shown that when e-beam dose levels are selected depending on the specific orientation of the device relative to the beam, there is a reduction in the overall variance as compared to using the same dose for each pass. FIGS. 5 and 6 show how a reduction in variance may be achieved by selecting a more appropriate density profile for the device. In this example the variance is dramatically reduced when the device is irradiated in three directions, as opposed to two.

Figure 3B:
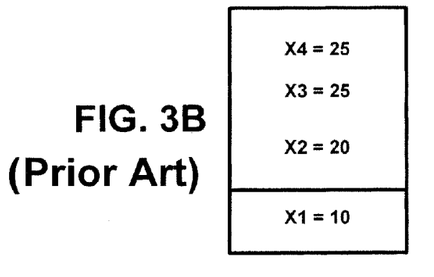
Figure 3C:
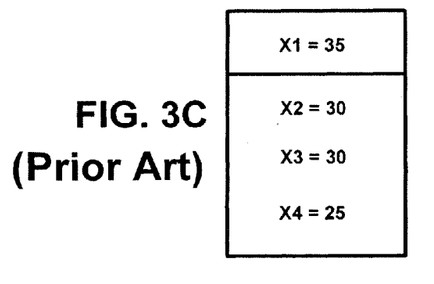
Figure 4A:
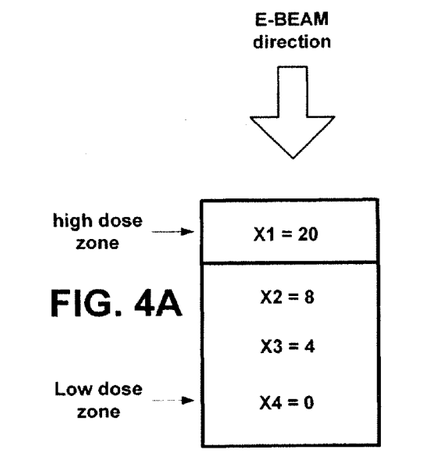

FIGS. 3A-3C and FIGS. 4A-4C depict the dose-depth distribution for a catheter (two-sided density profile) which is twice passed before the radiation source. The direction of the radiation beam is illustrated in FIGS. 3A and 4A and is the same for subsequent views FIGS. 3B 3C, 4B and 4C. The locations x1, x2, x3, and x4 indicate the depth-wise coordinates of a mass of material, e.g., a distal end of a catheter, corresponding to the indicated dose levels, e.g., in FIG. 3A location x1 has a dose level after the first pass of 25 KGy. The figures also identify low dose zones and high dose zones, as described earlier in connection with FIG. 1. For the first pass, location x1 is in a high dose zone, whereas in the second pass x4 is in the high dose zone.

Figure 4B:
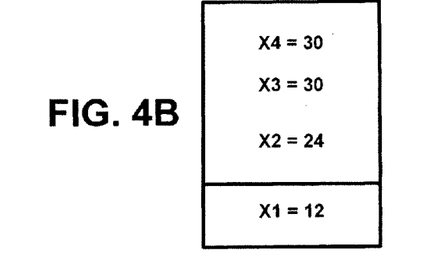
Figure 4C:
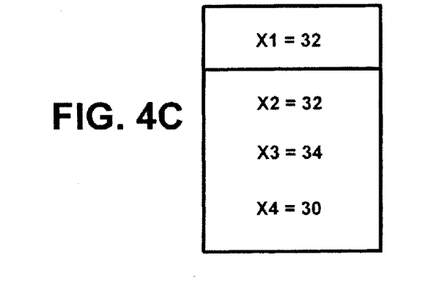

FIGS. 3A-3C illustrate the dose levels received at depths x1, x2, x3, and x4 when the component of, or the device is irradiated by a 25 KGy dose for both passes. FIGS. 4A-4C illustrate the dose levels received at depths x1, x2, x3, and x4 when the same device is irradiated, but with a 30 KGy dose for the first pass and a 20 KGy dose for the second pass (the first dose level is reduced relative to the second dose level because a first density of material in a high dose area for the first orientation is higher than a second density of material in a high dose area for the second orientation). For the second pass the device is flipped 180 degrees around, as can be inferred from the locations of x1, x2, x3 and x4 in the figures. FIGS. 3A and 4A show the dose levels after the first pass. The dose levels received when the device is flipped 180 degrees around is shown in FIGS. 3B and 4B. FIGS. 3C and 4C show the combined dose levels at each location x1, x2, x3, and x4 after both passes, obtained by summing the dose levels at each location for each pass. The reduction in variance in dosage levels made possible by the invention is seen in the comparison of the final dose levels in FIG. 3C with the final dose levels in FIG. 4C.

Assume the dose limit for the catheter of FIGS. 3 and 4 is 40 KGy before radiation damage occurs and the minimum dose level for SAL $10^{-6}$ is 25 KGy. As can be understood by comparing the dose levels at x1 to x4 in FIG. 3C, the variance in dose levels when the same dose level (25 KGy) is applied is 10 KGy. The minimum dose level for SAL $10^{-6}$ (25 KGy) is reached in one location, while a maximum dose of 35 KGy is reached elsewhere. Thus, in order to everywhere adequately reduce the device's bio-burden an operator has only a 5 KGy operating range to work with (40−35=5 KGy).

This is a narrow operating range, which complicates the sterilization process, as explained earlier. Perhaps, more importantly, with only a 5 KGy upper operating range available, there is a greater risk that the device will become damaged, either because beam parameters are difficult to control within this operating range or the actual dosage received at a location is higher than what was predicted by, or inferred from the dose map.

FIG. 4C, by comparison, shows a more favorable dose variance of 4 KGy (compare x3 with x4) with the minimum dose level being 30 KGy and maximum dose being 34 KGy. Using the method of the invention, there is a lower operating range of 5 KGy and an upper operating range of 6 KGy. As the operating range is wider, it is more easy to control the beam to ensure a SAL without exceeding the upper limit of 40 KGy. The wider operating range also allows the operator to provide more space between the beam dose level and upper limit than in the case of FIGS. 3A-3C, so that he/she may account more for uncertainty in the actual dose levels received by the device.

FIGS. 5A-5C and FIGS. 6A-6B depict the dose-depth distribution for the device taking the shape of the disc in FIG. 2. As explained earlier, for radiation sterilization the disc is best viewed as a three-sided body when its denser components are arranged in this way, as will be more fully appreciated from the following discussion. FIGS. 5A-5C show dose levels after two passes at the same dose level. The device is flipped 180 degrees around after the first pass, which is typical in the art, regardless of the arrangement of the denser components in the device. As before the beam direction is shown, as is the dose level at depth-wise coordinates y1, y2, y3 . . . y6. A 25 KGy dose is applied for each pass. Referring to FIG. 5A, y1 is located in the high dose zone for the first pass. For the second pass y3, y4 and y5 are each located in the high dose zone (device is flipped 180 degrees between passes). FIGS. 6A-6B show the dose levels when the same device is, instead, exposed to radiation in three different orientations, each 120 degrees apart, with the same dose levels for each pass (17 KGy). Consistent with a three-sided density profile, there are three passes made. The beam direction is normal to the sides of the triangle in FIG. 6A, as indicated. In this example, the same dose level may be applied for each orientation. For medical devices having, or best approximated by a three-sided density profile, the dose levels can be different for each pass to minimize variances in dosage levels, as explained in greater detail below.

Assume the dose limit for the disc of FIGS. 5 and 6 is 50 KGy before radiation damage occurs and the minimum dose level for SAL $10^{-6}$ is 25 KGy. As can be understood by comparing the dose levels at y1 to y5 in FIG. 5C, the variance in dose levels when the same dose level (25 KGy) is applied is 20 KGy with the minimum dose level being 30 KGy and maximum dose being 50 KG, which is at the limit. Thus, in order to obtain a SAL $10^{-6}$ everywhere an operator, once again, has only a 5 KGy operating range to work with. FIG. 6B, by comparison, shows a far more favorable variance of only 0 KGy with the dose level being 37 KGy everywhere. Thus in practicing the method of the invention, in this case selecting orientations based on the device's density profile, there is an operating range of 25 KGy available, as compared with 5 KGy using existing techniques.

In the example just described, the same dose level is applied for each orientation. In the more general case, it will not be possible to have a density distribution that is so favorable to the objective of reducing variance as in the case of the disc of FIG. 2. The components are more dispersed, so that a density profile can only roughly approximate the distribution by a polygon. In these cases, one may increase the number of passes, e.g., 4, 5, 6, or more to reduce variance. Furthermore, each pass may have its own, unique dose level selected to minimize the sum total variance after all passes before the radiation source are made, although as the above example shows, it is contemplated that for some devices proper selection of the orientations may obviate the need to adjust the dose level for each pass, which is desirable.

The minimization may be based on a variance over all locations selected for the dose map, or the locations where the maximum and minimum occurred. Thus, the dose levels for each pass, and/or the number of passes may be selected in order to minimize the difference between a first dosimeter location (predicting the dosage level of the device near a first device location) and a second dosimeter location (predicting the dosage level of the device near a second device location). Or the dose levels for each pass, and/or the number of passes may be selected to minimize the dosage variance across or over all dosimeters making up the dose maps, i.e., minimize the variance over the entire device, as opposed to, for example, only two locations on the device.

For a device subject to four passes, four dose maps are constructed to determine the distribution over the device for four orientations, e.g., 90 degree rotations, and then a dose level is calculated for each pass to minimize the total variance over the device after all four passes are complete. Similarly, for six passes six dose maps are constructed to determine the distribution over the device for each of the six orientations, e.g., 60 degree rotations, and then a dose level is calculated for each pass to minimize the total variance over the device after all six passes are complete.

In the more general case, as the number of passes becomes "n" for "m" dosimeter locations in the dose map, the solution to the mathematical problem of solving for the dose levels becomes one of n unknowns to solve for using a set of m linear equations, e.g., each of the m equations may, at least initially, be expressed, in terms of each of the n unknowns (dose levels) as the summation of the dose levels at each of the m dosimeter locations. The resulting equations (e.g., differences in total dosage between dosimeter locations) would in general define an over-determined set of equations to solve for the dose levels (since there can be more dosimeter locations than passes before the radiation source, there are more equations than unknowns to solve for). This assumes, of course, that each equation is linearly independent of the other equations. Notably, it is believed that if equations are linear dependant, this may provide insight into the density profile for the device, as linear interdependency suggests that less passes before the radiation source are sufficient because it should produce the same result. As will be appreciated, the mathematical formulation and solution to minimization of variance problems similar to these just proposed are well known in the art.

Figure 7:
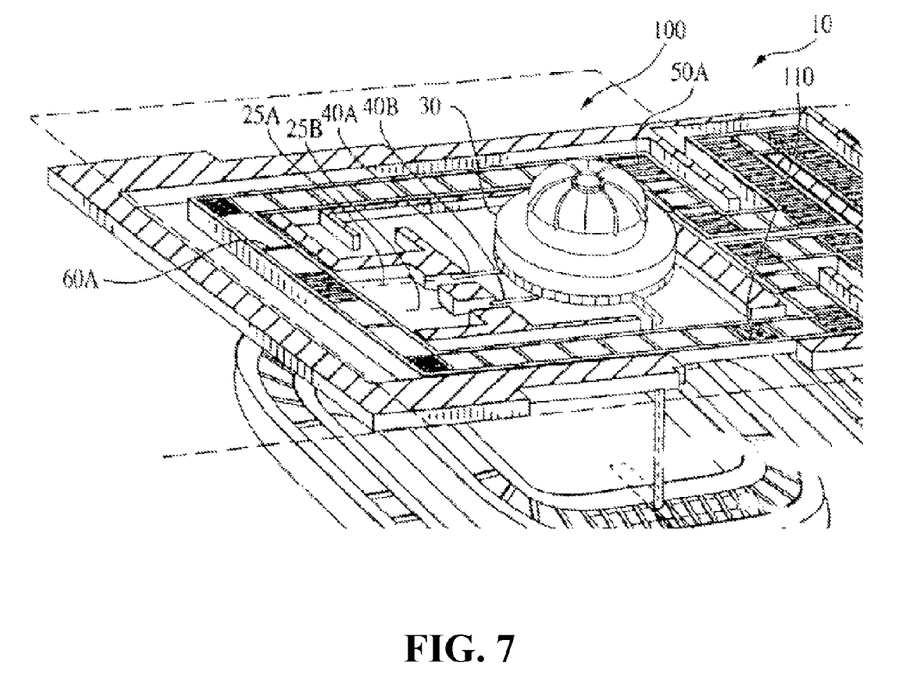
FIG. 7 is an illustrative radiation apparatus.

FIG. 7 illustrates an irradiation apparatus 10. A radiation source 30 contains radiation beam paths 40A and 40B, which project radiation beams 25A and 25B, respectively. A conveyor system 50A contains a beam pass conveyor 60A that conveys product through either x-ray beam 25A or 25B. A conveyor system 50A contains beam pass conveyor 60A that conveys product through either beam 25A or 25B. Beam paths 40A and 40B are positioned adjacent and perpendicular to the direction of travel on beam pass conveyor 60A. An active or passive rotation device 110 is located at some point after the beam pass conveyor 60A. Item 100 is a radiation cell.

While particular embodiments of the present invention have been shown and described, it will be apparent to those skilled in the art, with the benefit of having read this disclosure, that changes and modifications can be made without departing from this invention in its broader aspects.

What is claimed is:

1. A method for sterilizing medical devices by irradiation, comprising:
   determining radiation dose levels to apply to each of the medical devices, including
      providing at least a first dose map and a second dose map for one of the medical devices, the first and second dose maps representing a distribution of received radiation over the medical device when the medical device is orientated in at least a first direction and a second direction, respectively, relative to a radiation source, wherein the first and second directions are determined from a density profile of the medical device, and
      computing a first dose level and a second dose level from the first and second dose maps and satisfying (a), (b) and (c):
         (a) the sum total of the computed first and second dose levels achieves a sterility assurance level (SAL) for the medical device,
         (b) the sum total of the computed first and second dose levels is less than a dose level causing damage to the medical device, and
         (c) when the medical device is irradiated using the first and second dose levels, the difference in the sum total of radiation received at a first location and a second location on the medical device is a minimum for the medical device orientated in the respective first direction and second direction relative to the radiation source; and
   exposing each of the medical devices to the first dose level when oriented in the first direction and the second dose level when oriented in the second direction;
   wherein the first dose level is different from the second dose level.

2. The method of claim 1, wherein the medical device is a catheter including a drug-eluting bio-absorbable polymer.

3. The method of claim 1, wherein e-beam radiation is used.

4. The method of claim 2, wherein the first dose level is reduced relative to the second dose level when a first density of material in a high dose area for the first orientation is higher than a second density of material in a high dose area for the second orientation.

5. The method of claim 1, wherein the exposing step includes moving each of the medical devices along a conveyor at a predetermined rate based on the desired dose level, wherein the first dose level is applied during the first pass, the medical devices are re-orientated then the second dose level is applied during the second pass.

6. A system for sterilizing medical devices by irradiation, comprising:
   a radiation source;
   a conveyor system for moving the medical devices before the radiation source in conjunction with dose levels of radiation desired per medical device;
   providing at least a first and second dose level to use when a medical device is, respectively, orientated in at least a first and second direction on the conveyor before the radiation source,
   wherein
      the first and second directions are determined from a density profile of the medical device,
      the dose levels are different from each other,
      the dose levels are selected so that a difference in total radiation between a first location and a second location on the medical device is minimized,
      the sum total of the first and second dose levels achieves a sterility assurance level (SAL) for the medical device, and
      the sum total of the first and second dose levels is less than a dose level causing damage to the medical device; and
   wherein the system is configured for sterilizing the medical devices including exposing the medical devices to the first dose level when orientated in the first direction, and exposing the medical devices to the second dose level when oriented in the second direction.

7. The system of claim 6, wherein the dose level causing damage to the medical device is above 30 kGy.

8. The system of claim 6, wherein the first dose level is ⅔ of the second dose level.

9. The system of claim 6, wherein e-beam radiation is used.

10. The system of claim 6, wherein the medical device comprises a catheter including a drug-eluting bio-absorbable polymer.

11. A method for sterilizing medical devices by irradiation, comprising:
   providing a dose map for each of at least a first and second orientation of a medical device relative to a radiation source, the first and second orientations having been determined from a density profile of the medical device;
   increasing an available operating range for irradiating the medical device including computing, using the dose maps for the medical device, at least a first dose level and a second dose level satisfying (a), (b) and (c):
      (a) the sum total of the computed first and second dose levels achieves a sterility assurance level (SAL) for the medical device,
      (b) when the medical device is irradiated using the first and second dose levels, the difference in the sum total of radiation received at a first location and a second location on the medical device is a minimum for the medical device positioned in the respective first orientation and second orientation, and
      (c) the sum of the at least first and second doses is less than a radiation dose that damages the medical device; and
   exposing each of a plurality of the medical devices to the first dose level when positioned in the first orientation and the second dose level when positioned in the second orientation; and
   wherein the first dose level is different from the second dose level.

12. The method of claim 11, wherein the maximum radiation dosage is 30 kGy and the minimum radiation dosage for achieving SAL is 25 kGy.

* * * * *